United States Patent [19]
Karkanen

[11] Patent Number: 6,013,009
[45] Date of Patent: Jan. 11, 2000

[54] WALKING/RUNNING HEART RATE MONITORING SYSTEM

[76] Inventor: Kip Michael Karkanen, 256 Castle Glen Rd., Walnut Creek, Calif. 94595

[21] Appl. No.: 08/815,127

[22] Filed: Mar. 11, 1997

Related U.S. Application Data

[60] Provisional application No. 60/013,176, Mar. 12, 1996.
[51] Int. Cl.$^7$ .................................................. A61B 5/04
[52] U.S. Cl. .................... 482/9; 482/8; 482/901; 607/19
[58] Field of Search .............. 482/1–9, 51, 54, 482/57, 900–902; 601/23; 607/9, 17–19

[56] References Cited

U.S. PATENT DOCUMENTS

| | | |
|---|---|---|
| 3,511,097 | 5/1970 | Corwin . |
| 3,767,195 | 10/1973 | Dimick . |
| 3,984,666 | 10/1976 | Barron . |
| 4,101,071 | 7/1978 | Brejnik et al. . |
| 4,159,416 | 6/1979 | Brejnik et al. . |
| 4,192,000 | 3/1980 | Lipsey . |
| 4,358,105 | 11/1982 | Sweeney, Jr. . |
| 4,367,752 | 1/1983 | Jiminez et al. . |
| 4,380,802 | 4/1983 | Segar et al. . |
| 4,434,801 | 3/1984 | Jiminez et al. . |
| 4,457,310 | 7/1984 | Swyer et al. . |
| 4,566,461 | 1/1986 | Lubell et al. . |
| 4,855,942 | 8/1989 | Bianco . |
| 5,067,710 | 11/1991 | Watterson et al. ........................... 482/3 |
| 5,527,239 | 6/1996 | Abbondanza ............................... 482/8 |
| 5,618,245 | 4/1997 | Trulaske et al. ............................ 482/7 |

FOREIGN PATENT DOCUMENTS

0 119 009 A1  9/1984  European Pat. Off. .

Primary Examiner—Glenn E. Richman
Attorney, Agent, or Firm—Richard C. Litman

[57] ABSTRACT

A process of using a heart rate monitor to construct a user's personal heart rate curve, and using the heart rate curve to forecast the user's personal caloric expenditure on the basis of the user's heart rate while walking or running. A sub-unit installed within or otherwise connected to the electronic circuitry of a conventional heart rate monitor operates under control of a microprocessor. The sub-unit receives exogenous inputs by the user for conducting various calculations from a plurality of test data which is stored in memory by the user. The sub-unit utilizes the test data to calculate a rate of calories burned per pound for each test exercise, where the calculation is performed using a pre-programmed formula which differs according to the form of exercise. Next the sub-unit calculates a rate of calories burned per minute for each test exercise by multiplying the user's weight by the previously calculate rate per pound. Finally, the sub-until applies a least squares linear regression algorithm for measuring calories per minute against heartbeats per minute for the plurality of test exercises, thereby producing a user's heart rate curve for a particular form of exercise. During later exercise, output signals from the heart rate monitor regarding current heart rate, average heart rate, and the total elapsed time during exercise are used to calculate and output the current calories per minute expenditure, average calories per minute expenditure, and total calories expended for each exercise session.

19 Claims, 4 Drawing Sheets

CALCULATIONS

RATE (CAL/MIN) = RATE PER POUND x WEIGHT
HEART RATE CURVE (CAL/MIN) = A'+B'xENDING HEART RATE(bpm)
CURRENT RATE (CAL/MIN) =
HEART RATE CURVE (CAL/MIN) x CURRENT HEART RATE
AVERAGE RATE (CAL/MIN) =
HEART RATE CURVE (CAL/MIN) x AVERAGE HEART RATE
TOTAL CALORIES (CAL) =
AVERAGE RATE x TOTAL ELAPSED TIME
MINIMUM HEART RATE LIMIT = .55x(220-AGE)
MAXIMUM HEART RATE LIMIT = .90x(220-AGE)

OUTPUT SIGNALS

FIG.2B

WALKING/RUNNING HEART RATE MONITORING SYSTEM

CROSS REFERENCE TO RELATED APPLICATIONS

This application claims the benefit of U.S. Provisional application Ser. No. 60/013,176, filed Mar. 12, 1996.

BACKGROUND OF THE INVENTION

1. Field of the Invention

The present invention relates to a sub-unit for use within conventional heart rate monitors where the sub-unit receives pre-existing output signals from the heart rate monitor to permit a user to construct a personal heart rate curve for walking or running in order to forecast personal caloric expenditure on the basis of the user's heart rate while walking or running. The present invention also relates to a process for using the sub-unit to forecast personal caloric expenditure on the basis of the user's heart rate while walking or running.

2. Description of the Relevant Art

People who exercise and diet to lose weight and achieve a particular level of fitness have not had an accurate means of monitoring their progress, except by using exercise machines such as computerized treadmills. The present invention enables; people to use a heart rate monitor to measure their progress while exercising by walking or running.

U.S. Pat. No. 3,511,097, issued on May 12, 1970 to Gilbert Corwin discloses an exercise bicycle which tells the user how many calories he or she is burning while pedalling. Mechanical energy from pedalling is transformed into output electrical signals using an attached generator. The instant invention may be distinguished in that it involves walking and running. It further may be distinguished in that it uses output signals from a heart rate monitor to forecast calories burned.

U.S. Pat. No. 3,767,195, issued on Oct. 23, 1973, to Keene Paul Dimick, discloses a programmed bicycle exerciser which automatically varies user load at the pedals and displays user mechanical energy burned and heart rate. The instant invention involves running and walking, rather than bicycling, and forecasts human energy burned based on a predetermined relationship between calories and an individual's heart rate.

U.S. Pat. No. 3,984,666 issued on Oct. 5, 1976, Benjamin Barron discloses an exercise device which measured variable mechanical energy output from an exercising human and calculates calories expended using analog circuitry. The instant invention does not directly convert mechanical energy output to calories consumed by a human but rather forecasts human energy consumption directly using predetermined human walking and running equations and related individual heart rates.

U.S. Pat. No. 4,101,071, issued on Jul. 18, 1978, and U.S Pat. No. 4,159,416, issued on Jun. 26, 1979, both to Carl Brejnik and William T. Whitlow, disclose an electronic calorie counter, to be worn as a wrist watch, which includes a heart pulse detector and microcomputer, and displays time, pulse rate and calorie totals using a pre-constructed relationship between the user's heart rate and calories burned across the individual's entire heart rate range. The instant invention is distinguishable in that it constructs the individual's relationship between calories burned and heart rate for walking and running only, across a more restricted heart rate range.

U.S. Pat. No. 4,192,000, issued on Mar. 4, 1980 to Elmer M. Lipsey, discloses an electronic calorie counter which uses a vertical motion accelerator's output signals to forecast calories burned using sedentary, light, moderate, vigorous and severe human activity coefficients. The instant invention differs from Lipsey by forecasting walking and running calories using predetermined human energy equations and individual heart rates.

U.S. Pat. No. 4,358,105 issued on Nov. 9, 1982, to James S. Sweeney Jr. converts mechanical energy output to calories burned using a stationary cycle, assuming the energy output efficiency of the human operator is 20%, and is distinguishable from the instant invention in that no such conversion is made and the activity involves running and walking.

U.S. Pat. No. 4,367,752, issued on Jan. 11, 1983, to Oscar Jiminez and Frank J. Bianco discloses a device combining heart rate monitor, pedometer and various predetermined constants and fitness factors. Calories for walking or jogging are forecast by using the exercising heart rate scaled against the resting heart rate. The fitness factors are derived from tables after the individual takes a 12 minute maximum aerobic capacity test. The instant invention is distinguishable in that it uses running and walking speeds with a pre-existing heart rate monitor to construct a direct relationship between the individual's running and walking calories and heart rate without the need for fitness factors or heart rate scaling. The individual does not take a maximum aerobic capacity test which is dangerous and except for the very fit should be conducted under medical supervision. The instant invention is suitable for use by persons at all fitness levels.

U.S. Pat. No. 4,380,802 issued on Apr. 19, 1983 to Richard B. Segar and Lewis C. Marascalco, discloses an electronic calorie counter, in which data about foods eaten and exercises performed is inputted by the user, and the device outputs an estimate of the difference between the calories gained from the food and lost from exercise. The instant invention is distinguished from the present invention in that monitoring the user's heart rate is used.

U.S. Pat. No. 4,434,801 (a CIP of the '752 patent discussed supra), issued on Mar. 6, 1984 to Oscar Jiminez and Frank J. Bianco, discloses an apparatus for testing the physical condition of a self propelled vehicle rider which includes monitoring the rider's heart rate and speed. The instant invention does not involve cycling, only running and walking.

U.S. Pat. Mo. 4,457,310, issued on Jul. 3, 1984 to Paul R. Swyer, Tibor Heim, and John M. Smith discloses a method and apparatus for determining the energy requirements of newborns, based on their heart rates. They use a predetermined heart rate-energy consumption relationship for newborns all with similar weights and fitness levels, resting in a hospital ward. The instant invention determines the individual heart rate-energy relationship of individual adults who have varying degrees of weight and fitness.

U.S. Pat. No. 4,566,461 issued on Jan. 28, 1986, Michael Lubell and Stephen Marks, discloses a device used in running and cycling whereby the exercising heart rate is monitored and then linearly scaled between the subjects resting and maximum heart rate to estimate calories. A maximum aerobic capacity test is required at maximum heart rate to forecast calories which except for the very fit should be conducted under medical supervision. The instant invention is distinguished by not requiring a maximum aerobic capacity test and by not using a linear extrapolation between resting and maximal heart rate. The instant invention moreover limits calorie forecast to a narrower heart rate range comprising 55% to 90% of the subject's maximum heart rate.

U.S. Pat. No. 4,855,942 issued on Aug. 8, 1989, to Frank J. Bianco discloses a microcomputer enclosed in a watch case which estimates calories consumed by the wearer by measuring the motion of the wearer. It is distinguishable from the instant invention as it does not involve monitoring the wearer's heart rate.

European Pat. Application Publication No. 0 119 009 published Sep. 19, 1984, for an invention by Edward C. Frederick, discloses a device for determining the speed, distance traversed, time and calories expended by a runner. It consists of a pressure sensor in the runner's shoe, which sends a radio signal received by a device that may be worn around the runner's wrist, such as a watch, which contains a microprocessor. Unlike the instant invention, it does not monitor or determine heart rate.

None of the above inventions and patents, taken either singly or in combination, is seen to describe the instant invention as claimed.

SUMMARY OF THE INVENTION

The present invention is a process of using a heart rate monitor to construct a user's personal heart rate curve, and using the heart rate curve to forecast the user's personal caloric expenditure on the basis of the user's heart rate while walking or running. To achieve the desired process, a sub-unit will be installed within or otherwise connected to the electronic circuitry of a conventional heart rate monitor, operating under control of a microprocessor which may control the heart rate monitor and the sub-unit, or the sub-unit alone. The microprocessor executes a stored program for performing the process of the present invention. Performance of operations which involve the sub-unit, however, necessarily require the use of data entry means such as a keypad or the like, a memory storage device of a suitable size for the storage of data, a display such as a liquid crystal display (LCD) or the like, and a power source such as a battery.

The present invention involves the use of data from a plurality of test exercises to create a personal heart rate curve. Each test is performed at varying degrees of difficulty (i.e., walking between 1 and 5 miles per hour, or running between 3 and 14 miles per hour). By inputting into the sub-unit the speed and current heart rates for each test, as well as the user's age and weight, the sub-unit will calculate a rate of calories burned per pound for each test exercise. This calculation is performed using a predetermined formula which varies according to this form of exercise utilized by the user. According to one embodiment, where walking is the utilized exercise, the formula is:

Rate per Pound (Cal/lb-min=) $A+Bv+Cv^2+KDV^3$ where:

V=Walking Speed (mph)—limited to a minimum of 1 mph and a maximum of 5 mph

A=0.0195

B=−0.00436

C=0.00245

D=$[0.000801(W/154)^{0.425}]$/W/

W=Weight (lbs)

K=20 or 1 (0=Treadmill; 1=Outdoors) and where A, B, C and D are known predetermined constants based on a statistical sample of 2739 adults who walk normally between 1 mph to 5 mph. According to another embodiment, where running is the utilized exercise, the formula is:

Rate per Pound (Cal/lb-min)=$A+BV+CV^2+KDV^3$ where:

V=Running Speed (mph)—limited to a minimum of 3 mph and a maximum of 14 mph

A=0.0395

B=0.00327

C=0.000455

D=$[0.00801(W/154)^{0.425}]$/W

W=Weight (lbs)

K=0 or 1 (0=Treadmill; 1=Outdoors)

and where A, B, C and D are known predetermined constants based on a statistical sample of 2463 adults who run normally between 3 mph to 14 mph. Next the sub-unit calculates a rate of calories burned per minute for each test exercise by multiplying the users weight by the previously calculate rate per pound. Finally, the sub-unit applies a least squares linear regression algorithm for measuring calories per minute against heartbeats per minute for the plurality of test exercises, thereby producing a user's heart rate curve for a particular form of exercise (i.e., running or walking). Preferably, four such test exercises are performed.

During later exercise, output signals from the heart rate monitor will inform the sub-unit of the user's current heart rate, average heart rate, and the total elapsed time during exercise, With the above signals input into the sub-unit, the sub-unit will calculate and output the current calories per minute expenditure, average calories per minute expenditure, and total calories expended for each exercise session. Each of the above outputs are calculated by measuring the current heart rate and average heart rate against the user's personal heart rate curve.

The above calculations by the sub-unit will be accurate where the user exercises with his or her heart rate within a predetermined target heart rate range (between 55% and 90% of his or her maximum heart rate), which is calculated by the sub-unit based upon the user's age. Also, the above calculations are an unbiased estimate of caloric expenditure which are accurate within the user's heart rate range, with a margin of error of plus or minus 20% to 25% at a confidence level of 95%.

Thus, the present invention uses information from a heart rate monitor to enable a user to formulate a diet and exercise plan for maintaining weight or losing weight and getting physically fit. The invention also enables the user to relate his or her caloric burn rate to his or her aerobic capacity. This permits the user to know his or her intensity of exercising, thereby allowing the user to determine if he or she is exercising within his or her training limits.

Accordingly, it is a principal object of the invention to provide a means for a user to construct his or her own walking or running heart rate curve.

It is another object of this invention to use said constructed walking or running heart rate curve to use the user's heart rate to forecast calories expended continuously in real time while walking or running.

It is another object of the invention to provide a means for using said invention to assist the user in creating a plan for maintaining and losing weight.

It is a further object of the invention to provide a means for monitoring progress in achieving and maintaining physical fitness.

It is a further object of this invention to provide a means whereby users of all fitness levels can use the present invention.

It is a further object of this invention to provide a more accurate unbiased forecast of calories burned for walking and running.

It is a further object of this invention to use pre-existing heart rate monitors and their pre-existing output signals to forecast walking and running calories.

Still another object of the invention is to provide improved elements and arrangements thereof in a apparatus for the purposes described which is inexpensive, dependable and fully effective in accomplishing its intended purposes.

These and other objects of the present invention will become readily apparent upon further review of the following specifications and drawings.

DETAILED DESCRIPTION OF THE PREFERRED EMBODIMENTS

The present invention is a process of using a heart rate monitor to construct a user's personal heart rate curve, and using the heart rate curve to forecast the user's personal caloric expenditure on the basis of the user's heart rate while walking or running. To achieve the desired process, a sub-unit will be installed within or otherwise connected to the electronic circuitry of a conventional heart rate monitor. Thus, the sub-unit will operate under control of a first microprocessor present in the heart rate monitor or under a second microprocessor dedicated exclusively to control of the sub-unit processes. Regardless of which microprocessor controls operation of the process of the present invention, the controlling microprocessor will execute a stored program for performing the process of the present invention. Performance of operations which involve the sub-unit will necessarily require the use of data entry means such as a keypad or the like; a memory storage device of a suitable size for storage of data; a display such as a liquid crystal display (LCD) or the like; and a power source such as a battery. These components may either be provided by the heart rate monitor or separately available on the sub-unit, depending upon which microprocessor arrangement is used. These components are all of the type which are used within conventional heart rate monitors and other related devices, thus they are readily available from a number of manufacturers. Conventional heart rate monitoring devices also include monitoring components which monitor a use's a heart rate and provide signals to the microprocessor in response to the user's heart rate. With the use of a single microprocessor capable of performing all executed programs, the single microprocessor will receive signals from the monitoring components, process the signals and store the results as data within the memory, and execute the process of the present invention to forecast a user's caloric expenditure while running or walking. However, it is preferred to use a second microprocessor for executing the sub-unit processes, whereby the second microprocessor will receive output signals concerning the user's heart rate from the first microprocessor and the second microprocessor will utilize these output signals to forecast a user's caloric expenditure while running or walking.

Figure 1A:
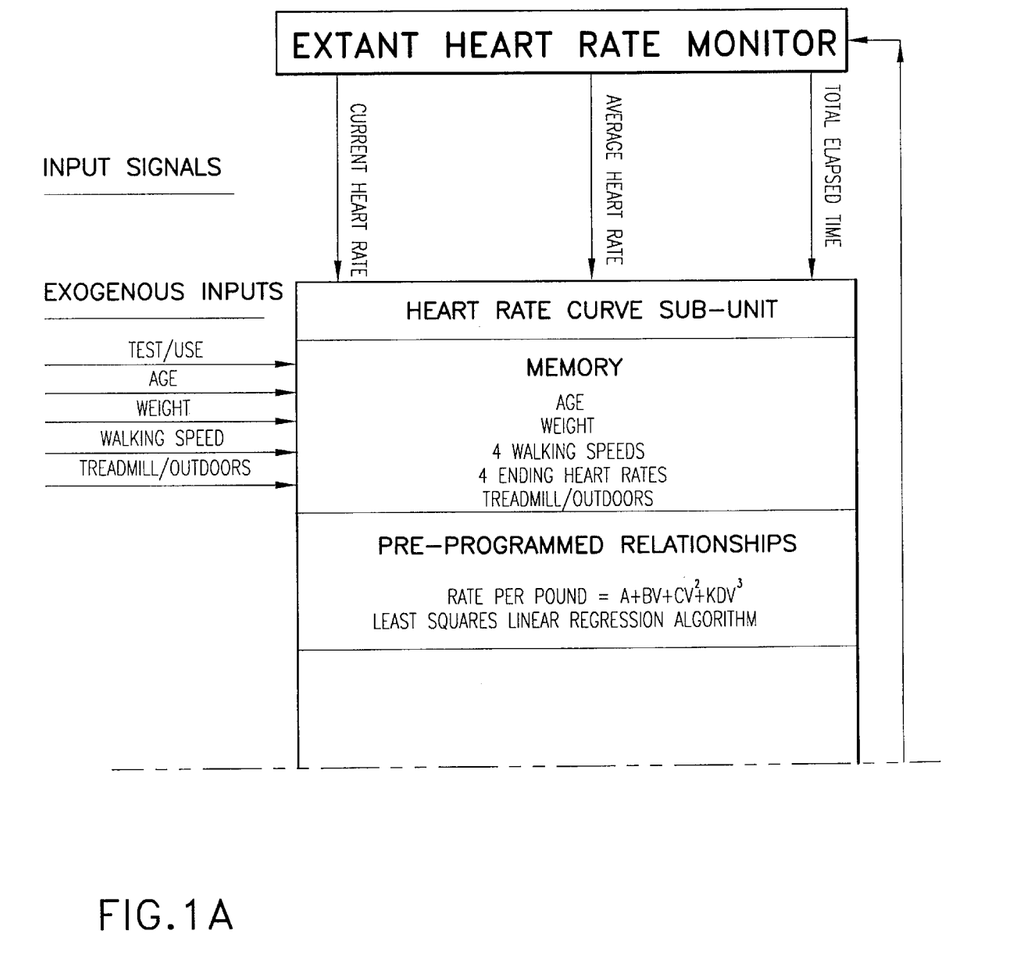
FIGS. 1A and 1B illustrate a flowchart of the system embodied in the present invention for a person who is exercising by walking.
Figure 1B:
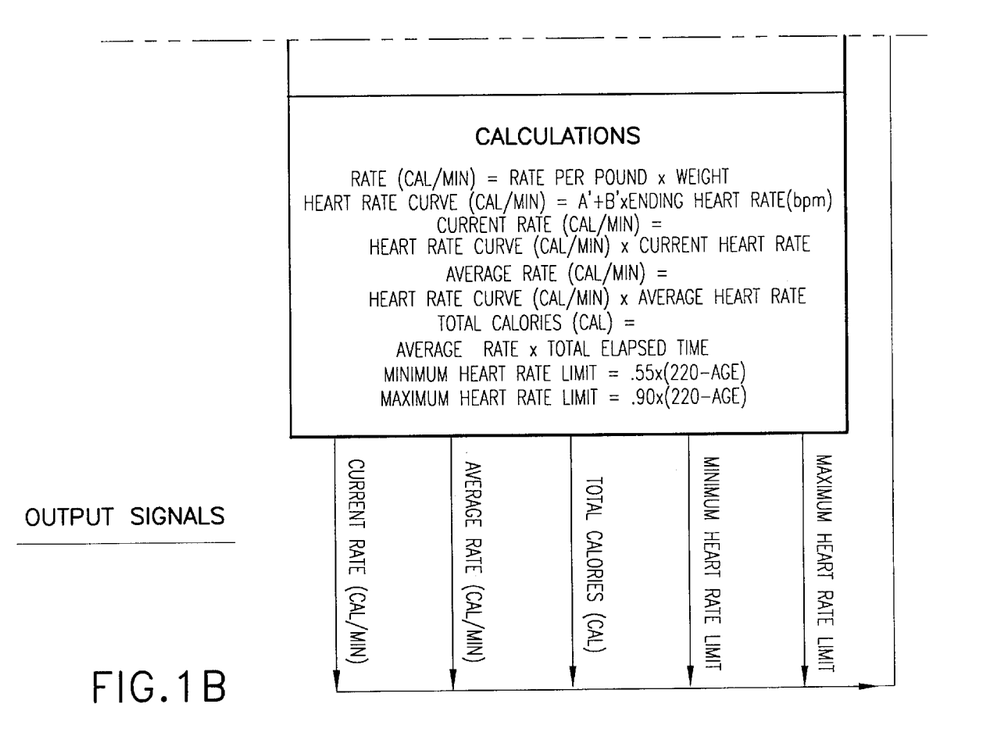

Referring to FIGS. 1A and 1B, a flowchart depicts the process of forecasting a user's caloric expenditure according to a first embodiment of the invention, where the user exercises by walking. Signals representing current heart rate, average heart rate, and total elapsed time are inputted from an extant heart rate monitor to a heart rate monitor sub-unit, either designed into the extant heart rate monitor or independently attached thereto as described above. Exogenous inputs to the sub-unit include a Test/Use signal which tells whether the monitor is being used to construct the user's heart rate curve for walking (e.g. Test mode) or whether the monitor is being used to forecast caloric expenditure (e.g. Use mode). Exogenous inputs to the sub-unit also include the user's age, weight, walking speed, and whether the user is walking outdoors or on a motorized treadmill. These exogenous inputs may be entered manually by the user with use of the data entry means provided on the heart rate monitor or sub-unit.

To construct the user's heart rate curve for walking, the user selects the Test mode, enters either Treadmill or Outdoors, and then enters his or her Age and Weight. Then the user walks at a constant known speed for 3 minutes on either a Motorized Treadmill, or Outdoors in still air and on hard surfaces such as asphalt or concrete. At the end of three minutes, he or she records his or her Current Heart Rate by storing it along with the corresponding speed in memory. This process is repeated 4 times for 4 different speeds such that at the completion of the test the stored variables are:

Variables Stored in Memory of Sub-Unit (a) Treadmill/Outdoors
(b) Age (yrs)
(c) Weight (lbs)
(d) Current Heart Rate (beats per minute)—Four values at 4 Walking Speeds
(e) Walking Speed (mph)—Four values between 1 mph and 5 mph corresponding to the 4 Current Heart Rate values.

After four data points (e.g. Current Heart Rate a corresponding Walking Speed) are input, a preprogrammmed relationship between calories burned and walking speed is used.

Preprogrammed Relationship in Sub-Unit (1) Rate per Pound $(Cal/lb\text{-}min) = A + BV + CV^2 + KDV^3$
where:

V=Walking Speed (mph)—limited to a minimum of 1 mph and a maximum of 5 mph [variable (e)]
A=0.0195
B=−0.00436
C=0.00245
D=$[0.000801(W/154)^{-425}]/W$
W=Weight (lbs) [variable (c)]
K=0 or 1 (0=Treadmill; 1=Outdoors) [variable (a)] and where A, B, C and D are known predetermined constants based on a statistical sample of 2739 adults who walk normally between 1 mph to 5 mph. Equation (1) is applicable to all individuals; who are between the ages of 17 to 60 years and who weigh between 100 to 300 pounds.

By multiplying the results of this relationship by the individual's Weight [variable (c)], the number of calories burned at each speed are calculated and stored in memory.

| |
|---|
| Calculation Stored in Memory in Sub-Unit |
| (2) Rate (Cal/min) = [Equation 1]<br>Rate per Pound (Cal/lb-min) ×<br>Weight (lbs) [variable (c)] |

With data concerning the number of calories burned at each speed stored in memory, a least squares linear regression of the four Rate values [equation (2)] against the four Current Heart Rate values [variables (d)] is calculated. This least squares relationship is preprogrammed in the sub-unit and computes the following relationship:

Preprogrammed Relationship in Sub-Unit (3) Heart Rate Curve (Cal/min)=A'+B'×Current Heart Rate (bpm)

where A' and B' are constants determined by the regression calculation and are applicable only to that individual at his current level of fitness for walking only. A' represents the y-intercept of the walking heart rate curve and B' represents the slope.

The individual's heart rate range for which this linear relationship holds as defined by equation (3) is between 55% and 90% of his or her maximum heart rate. His or her maximum heart rate is determined by subtracting Age in years [variable (b)] from 220. The limits to the heart rate curve for walking are calculated as follows:

(4) Minimum Heart Rate Value=0.55×(220—Age)

(5) Maximum Heart Rate Value=0.90×(220—Age)

Once calculated, these values are stored in the memory of the sub-unit.

After the individual user finishes constructing his or her heart rate curve for walking, as defined by equation (3) and limited to heart rates within the range defined by equations (4) and (5), the user should switch the sub-unit function to Use mode. In Use mode, the relationship denoted by equation (3) and limited to a range defined by equations (4) and (5) is used to produce a continuous real time readout of actual calories being burned (Cal/min) by the user according to his or her Current Heart Rate input signal from the extant heart rate monitor. Combined with the Time input signal from the extant heart rate monitor, Total Calories (Cal) are computed at any time using the Average Heart Rate signal for current or future walking trips.

Output Signals from Sub-Unit (6) Current Rate (Cal/min)=Heart Rate Curve×Current Heart Rate (7) Average Rate (Cal/min)=Heart Rate Curve×Average Heart Rate (8) Total Calories (Cal)=Average Rate (Cal/min)×Total Time (min)

All output signals from the sub-unit comprising Current Rate (Cal/min), Average Rate (Cal/Min), Total Calories (Cal), Minimum Heart Rate (bpm) and Maximum Heart Rate (bpm) are displayed on the extant heart monitor display or sub-unit display.

The heart rate curve for walking can be used at any time to forecast calories burned by walking and its use is not limited in time as long as the user's fitness level or weight do not materially change. The heart rate curve as defined by equation (3) is accurate within the user's heart rate range as defined by equations (4) and (5) with a margin of error of plus or minus 20% to 25% at a confidence level of 95% and is an unbiased estimate. When the user notices a change in his or her fitness level, it is appropriate to recalibrate the sub-unit by repeating the above-described steps to create a new Heart Rate Curve, as defined by equation (3).

Figure 2A:
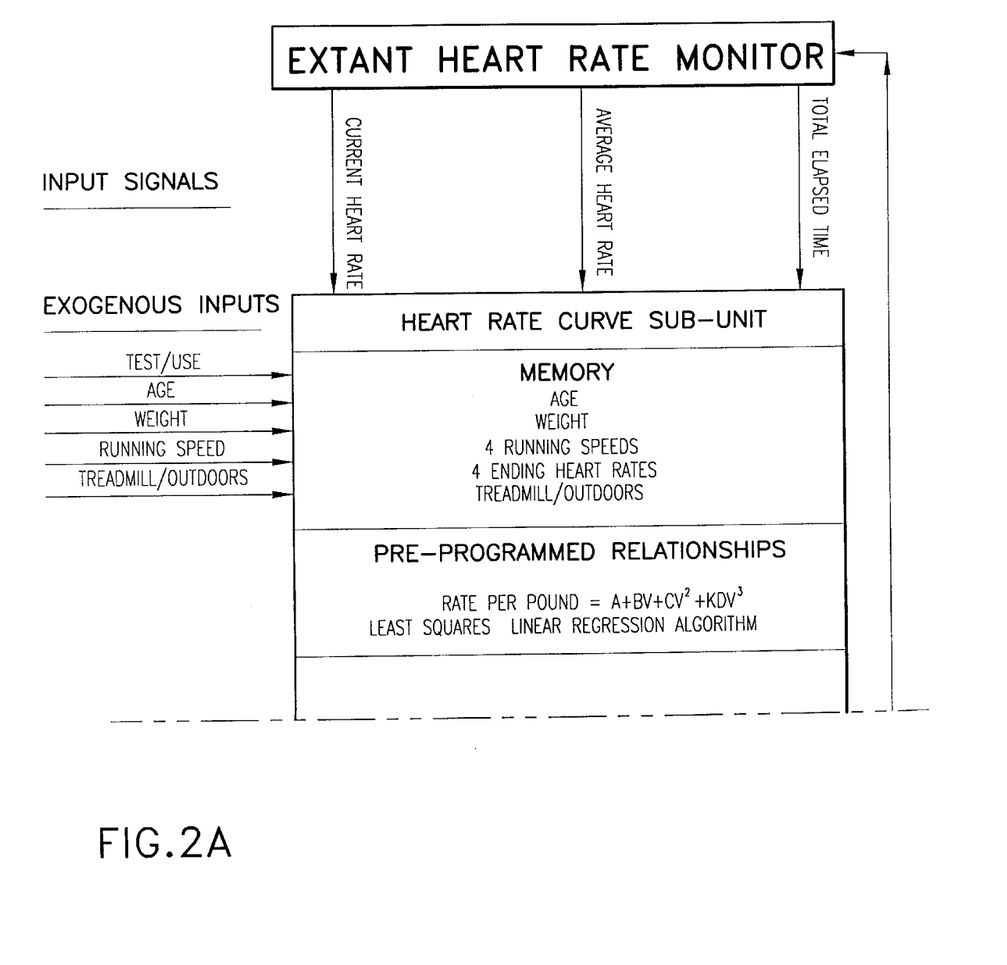
FIGS. 2A and 2B illustrate a flowchart of the system embodied in the present invention for a person who is exercising by running.
Figure 2B:
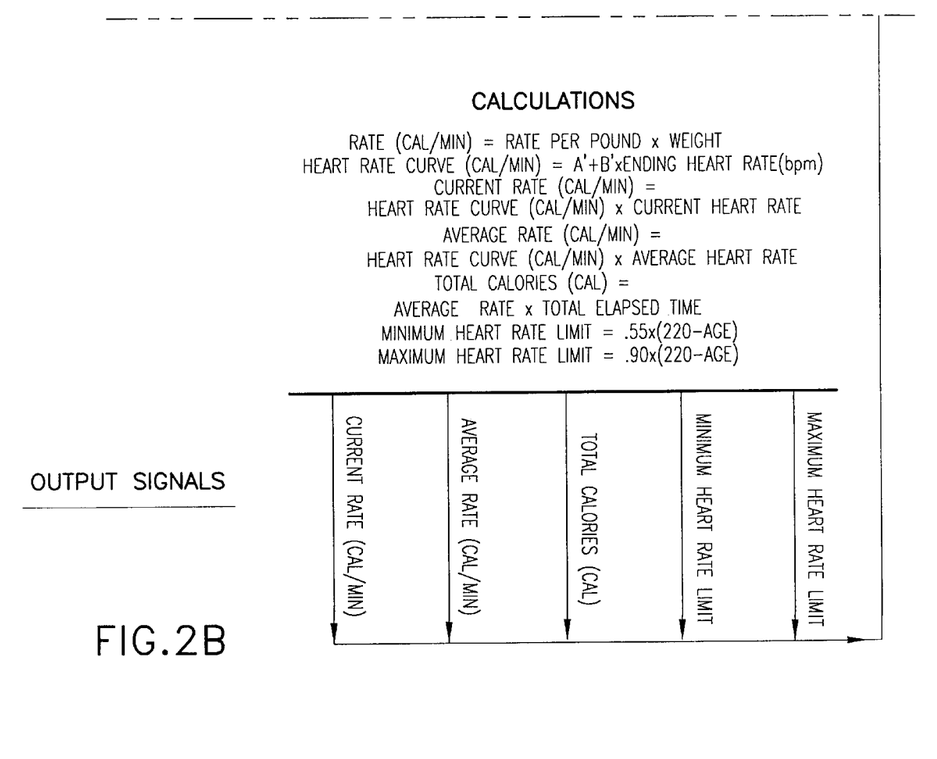

Referring to FIGS. 2A and 2B, a flowchart depicts the process of forecasting a user's caloric expenditure according to a first embodiment of the invention, where the user exercises by running. Signals representing current heart rate, average heart rate, and total elapsed time are inputted from an extant heart rate monitor to a heart rate monitor sub-unit, either designed into the extant heart rate monitor or independently attached thereto. Exogenous inputs of the sub-unit include those described above: a Test/Use signal, the user's age, weight, and running speed, and whether user is running outdoors or on a motorized treadmill. These exogenous inputs may be entered manually by the user with the of the data entry means provided on the heart rate monitor or sub-unit.

To construct the user's heart rate curve for running, the user selects the Test mode and either Treadmill or Outdoors and then enters his or her Age and Weight. Then the user runs at a constant known speed for 3 minutes on either a Motorized Treadmill, or Outdoors in still air and on hard surfaces such as asphalt or concrete. At the end of three minutes, he or she records his or her Current Heart Rate by storing it along with the corresponding speed in memory. This process is repeated four times for four different speeds such that at the completion of the test the stored variables are:

Variables Stored in Memory of Sub-Unit (a) Treadmill/Outdoors (b) Age (yrs)

(c) Weight (lbs)

(f) Current Heart Rate (beats per minute)—Four values at 4 Running Speeds (g) Running Speed (mph)—Four values between 3 mph and 14 mph corresponding to the 4 Current Heart Rate values.

After four data points (e.g. Current Heart Rate and corresponding Running Speed) are inputted, a preprogrammed relationship between calories burned and running speed is used Preprogrammed Relationship in Sub-Unit (9) Rate per Pound (Cal/lb-min) $A+BV+CV^3+KDV^3$ where:

V=Running Speed (mph)—limited to a minimum of 3 mph and a maximum of 14 mph [variable (g)]

A=0.0395

B=0.00327

C=0.0455

D=$[0.000801(W/154)^{0.425}]/W$

W=Weight (lbs) [variable (c)]

K=0 or 1 (C=Treadmill; 1=Outdoors) [variable (a)]

and where A, B, C and D are known predetermined constants based on a statistical sample of 2463 adults who run normally between 3 mph to 14 mph. Equation (9) is applicable to all individuals who are between the ages of 17 to 60 years and who weigh between 100 to 300 pounds.

By multiplying the results of this relationship by the individual's, Weight [variable (c)], the number of calories burned at each speed is calculated and stored in memory.

| | |
|---|---|
| (10) | Calculation Stored in Memory in Sub-Unit<br>Rate (Cal/min) =<br>Rate per Pound (Cal/lb-min) ×<br>Weight (lbs) [variable (c)] [Equation 9] |

With data concerning the number of calories burned at each speed stored in memory, a least squares linear regression of the four Rate values [equation (10)] against the four Current Heart Rate values is calculated [variable (f)]. This least squares relationship is preprogrammed in the sub-unit and computes the following relationship:

Preprogrammed Relationship in Sub-Unit (11) Heart Rate Curve (Cal/min)=A"+B"×Current Heart Rate (bpm) where A" and B" are constants determined by the regression calculation and are applicable only to that individual at his current level of fitness for running only. A" represents the y-intercept of the running heart rate curve and B" represents the slope.

The individual's heart rate range for which this linear relationship holds as defined by equation (11) is between 55% and 90% of his or her maximum heart rate. His or her maximum heart rate is determined by subtracting age in years [variable (b)] from 220. The limits to the heart rate curve for running are calculated as follows:

(12) Minimum Heart Rate Value=0.55×(220—Age)

(13) Maximum Heart Rate Value=0.90×(220—Age)

Once calculated, these values are stored in the memory of the sub-unit.

After the individual user finishes constructing his or her heart rate curve for running, as defined by equation (11) and limited to heart rates within the range defined by equations (12) and (13), the user should switch the sub-unit function to Use mode. In Use mode, the relationship denoted by equation (11) and limited to a range defined by equations (12) and (13) is used to produce a continuous real time readout of actual calories being burned (Cal/min) by the user according to his or her Current Heart Rate input signal from the extant heart rate monitor. Combined with the Time input signal from the extant heart rate monitor, Total Calories (Cal) are computed at any time using the Average Heart Rate signal for current or future running trips.

Output Signals from Sub-Unit (14) Current Rate (Cal/min)=Heart Rate Curve×Current Heart Rate (15) Average Rate (Cal/min)=Heart Rate Curve×Average Heart Rate (16) Total Calories (Cal)=Average Rate (Cal/min)×Total Time (min)

All output signals from the sub-unit comprising Current Rate (Cal/min), Average Rate (Cal/Min), Total Calories (Cal), Minimum Heart Rate (bpm) and Maximum Heart Rate (bpm) are displayed on the extant monitor display or sub-unit display.

The heart rate curve for running can be used at ante time to forecast calories burned by running, and its use is not limited in time as long as the user's fitness level or weight does not materially change. The heart rate curve as defined by equation (11) is accurate within the user's heart rate range as defined by equations (12) and (13) with a margin of error of plus or minus 20% to 25% at a confidence level of 95s. Moreover, the heart rate curve is an unbiased estimate. When the user notices a change in his or her fitness level, it is appropriate to recalibrate the sub-unit by repeating the above-described steps to create a new Heart Rate Curve, as defined by equation (11).

The above calculations were described only in connection to weight in unit pounds and velocities in miles per hour. It should be apparent to those skilled in the art that the calculations may also be achieved in unit kilograms and velocities in kilometers per hour by simply incorporating conversion factors into the formulas which respectively convert unit pounds into unit kilograms and unit miles into unit kilometers.

It is to be understood that the present invention is not limited to the embodiments described above, but encompasses any and all embodiments within the scope of the following claims.

I claim:

1. A process of using a sub-unit of a heart rate monitor to plan and monitor progress in achieving physical fitness through walking comprising:

inputting signals from a heart rate monitor to a sub-unit, the signals representing current heart rate, average heart rate, and total elapsed time;

inputting to the sub-unit a user's age, weight, walking speed and current heart rate from a plurality of walking tests:

calculating a rate of calories burned per pound of body weight for each of the plurality of walking tests using a formula as follows:

rate per pound=$A+BV+CV^2+KDV^3$, where A=0.0195, B=−0.00436, C=0.00245, and D=0.000801 $(W/154)^{0.425}/W$, where W=Weight (lbs), K=0 for Treadmill and K=1 for Outdoors and V=velocity of the user in miles per hour;

calculating a rate of calories burned per minute by multiplying the rate per pound by the user's weight; and outputting the values calculated.

2. The process of using a sub-unit of a heart rate monitor to plan and monitor progress in achieving physical fitness through walking according to claim 1, including:

applying a least squares linear regression algorithm for calories per minute against heartbeats per minute for the plurality of walking tests, the algorithm defining a heart rate curve.

3. The process of using a sub-unit of a heart rate monitor to plan and monitor progress in achieving physical fitness through walking according to claim 2, wherein the plurality of walking tests are performed at different velocities within the range of 1–5 miles per hour.

4. The process of using a sub-unit of a heart rate monitor to plan and monitor progress in achieving physical fitness through walking according to claim 3, wherein the plurality of walking tests includes at least three walking tests.

5. The process of using a sub-unit of a heart rate monitor to plan and monitor progress in achieving physical fitness, through walking according to claim 2, including:

calculating vertical coordinates for points on the heart rate curve in calories per minute, given horizontal coordinates in beats per minute, by multiplying a slope derived from the least squares linear regression by the current heart rates in beats per minute, and then adding a y-intercept from the regression.

6. The process of using a sub-unit of a heart rate monitor to plan and monitor progress in achieving physical fitness through walking according to claim 5, including:

determining a current rate of calories burned per minute from the heart rate curve using the current heart rate; and determining an average rate of calories burned per minute from the heart rate curve using the average heart rate.

7. The process of using a sub-unit of a heart rate monitor to plan and monitor progress in achieving physical fitness through walking according to claim 6, including:

calculating total calories burned by multiplying the average heart rate times the total elapsed time.

8. The process of using a sub-unit of a heart rate monitor to plan and monitor progress in achieving physical fitness through walking according to claim 1, including:

calculating a minimum heart rate in beats per minute as 55 per cent of a difference between 220 and the user's age in years; and calculating a maximum heart rate in beats per minute as 90 per cent of a difference between 220 and the user's age in years;

wherein the calculations for the current rate, the average rate, and the total calories burned are accurate for heart rates within the range between the minimum heart rate and the maximum heart rate.

9. A process of using a sub-unit of a heart rate monitor to plan and monitor progress in achieving physical fitness through running comprising:

inputting signals from a heart rate monitor to a sub-unit, the signals representing current heart rate, average heart rate, a total elapsed time;

inputting to the sub-unit a user's age, weight, running speed and current heart rates from a plurality of running tests:

calculating a rate of calories burned per pound of body weight for each of the plurality of running tests using a formula as follows:

rate per pound=$A+BV+CV^2+KDV^3$, where A=0.0395, B=0.00327, C=0.000455, and D=$0.000801(W/154)^{0.425}/W$, W=weight in pounds, K=0 for Treadmill and K=1 for Outdoors, and V=velocity of the user in miles per hour;

calculating a rate of calories burned per minute by multiplying the rate per pound times the user's weight; and outputting the values calculated.

10. The process of using a sub-unit of a heart rate monitor to plan and monitor progress in achieving physical fitness through running according to claim 9, including:

applying a least squares linear regression algorithm for calories per minute against heartbeats per minute for the plurality of running tests, the algorithm defining a heart rate curve.

11. The process of using a sub-unit of a heart rate monitor to plan and monitor progress in achieving physical fitness through running according to claim 10, wherein the plurality of running tests are performed at different velocities within the range of 3 14 miles per hour.

12. The process of using a sub-unit of a heart rate monitor to plan and monitor progress in achieving physical fitness through running according to claim 11, wherein the plurality of running tests includes at least three running teats.

13. The process of using a sub-unit of a heart rate monitor to plan and monitor progress in achieving physical fitness through running according to claim 10, including:

calculating vertical coordinates for points on the heart rate curve in calories per minute, given horizontal coordinates in beats per minute, by multiplying a slope derived from the least squares linear regression by the current heart rates in beats per minute, and then adding a y-intercept from the regression.

14. The process of using a sub-unit of a heart rate monitor to plan and monitor progress in achieving physical fitness through running according to claim 13, including:

determining a current rate of calories burned per minute from the heart rate curve using the current heart rate; and determining an average rate of calories burned per minute from the heart rate curve using the average heart rate.

15. The process of using a sub-unit of a heart rate monitor to plan and monitor progress in achieving physical fitness through running according to claim 13, including:

calculating total calories burned by multiplying the average heart rate by the total elapsed time.

16. The process of using a sub-unit of a heart rate monitor to plan and monitor progress in achieving physical fitness through running according to claim 9, including:

calculating a minimum heart rate in beats per minute as 55 per cent of a difference between 220 and the user's age in years; and calculating a maximum heart rate in beats per minute as 90 per cent of a difference between 220 and the user's age in years;

wherein the calculations for the current rate, the average rate, and the total calories burned are accurate for heart rates within the range between the minimum heart rate and the maximum heart rate.

17. A process of using a sub-unit of a heart rate monitor to measure caloric expenditure through exercise, comprising:

inputting signals from a heart rate monitor to a sub-unit, the signals representing current heart rate, average heart rate, and total elapsed time;

inputting to the sub-unit a user's age, weight, speed and current heart rates from a plurality of test exercises:

calculating a rate of calories burned per unit of body weight for each of the plurality of test exercises;

calculating a rate of calories burned per minute for each of the plurality of test exercises by multiplying the rate per unit weight by the user's weight;

applying a least squares linear regression algorithm for calories per minute against heartbeats per minute for the plurality of test exercises, the algorithm defining a heart rate curve;

calculating vertical coordinates for points on the heart rate curve in calories per minute, given horizontal coordinates in beats per minute, by multiplying a slope derived from the least squares linear regression by the current heart rates in beats per minute, and then adding a y-intercept from the regression; and outputting from the sub-unit a rate of calories burned per minute from the heart rate curve using one of the heart rate input signals.

18. A process of using a sub-unit of a heart rate monitor to measure caloric expenditure through exercise according to claim 17, wherein:

the exercise and each test exercise is walking; and the step of calculating a rate of calories burned per unit of body weight for each of the plurality of test exercises is performed by using a formula as follows:

rate per unit weight (in pounds)=$A+BV+CV^2+KDV^3$:

where $A=0.0195$, $B=-0.00436$, $C=0.00245$, and $D=0.000801(W/154)^{0.425}/W$, where W=Weight (lbs), K=0 for Treadmill and K=1 for Outdoors and V=velocity of the user in miles per hour.

19. A process of using a sub-unit of a heart rate monitor to measure caloric expenditure through exercise according to claim 17, wherein:

the exercise and each test exercise is running; and the step of calculating a rate of calories burned per unit of body weight for each of the plurality of test exercises by using a formula as follows:

rate per unit weight (in pounds)=$A+BV+CV^2+KDV^3$, where $A=0.0395$, $B=0.00327$, $C=0.000455$, and $D=0.00080(W/154)^{0.425}/W$, W=weight in pounds, K=0 for Treadmill and K=1 for Outdoors, and V=velocity of the user in miles per hour.

* * * * *